(12) United States Patent
Edie et al.

(10) Patent No.: US 7,998,210 B2
(45) Date of Patent: Aug. 16, 2011

(54) EXPANDABLE INTERVERTEBRAL SPACERS AND METHODS OF USE

(75) Inventors: Jason A. Edie, Salt Lake City, UT (US); Lloyd Guyton Bowers Cooper, Birmingham, AL (US); Don Byron Walker, II, Muscle Shoals, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/848,499

(22) Filed: Aug. 2, 2010

(65) Prior Publication Data

US 2010/0318189 A1    Dec. 16, 2010

Related U.S. Application Data

(63) Continuation of application No. 11/412,671, filed on Apr. 27, 2006, now Pat. No. 7,794,501.

(51) Int. Cl.
*A61F 2/44*    (2006.01)

(52) U.S. Cl. ............... 623/17.11; 623/17.12; 623/17.15
(58) Field of Classification Search ..... 623/17.11–17.16
See application file for complete search history.

(56) References Cited

U.S. PATENT DOCUMENTS

| 5,236,460 A * | 8/1993 | Barber ..................... 623/17.15 |
| 2008/0161933 A1 * | 7/2008 | Grotz et al. ................ 623/17.16 |

* cited by examiner

*Primary Examiner* — Eduardo C Robert
*Assistant Examiner* — Elana B Fisher (57) ABSTRACT

An intervertebral spacer for positioning between vertebral members. The spacer may include contact surfaces that are configured to contact against the vertebral members. A fluid cylinder may be positioned between the first and second contact surfaces and configured to contain a fluid. The fluid cylinder may include an outer cylinder with an open first end that telescopingly receives an inner cylinder. The spacer is configured to maintain the distance between the contact surfaces at a desired amount.

15 Claims, 7 Drawing Sheets

EXPANDABLE INTERVERTEBRAL SPACERS AND METHODS OF USE

RELATED APPLICATION

This application is a continuation of co-pending application Ser. No. 11/412,671 filed on Apr. 27, 2006 and herein incorporated by reference in its entirety.

BACKGROUND

The present application is directed to devices and methods for stabilizing vertebral members, and more particularly, to intervertebral implants and methods of use for replacing an intervertebral disc, vertebral member, or combination of both to distract and/or stabilize the spine.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to intervertebral spacers for positioning between first and second vertebral members. The spacer may include a first contact surface to contact the first vertebral member and a second contact surface to contact the second vertebral member. The spacer may include a fluid chamber positioned between the contact surfaces and have telescoping inner and outer members with the outer member having a first sidewall and being sized to receive the second member. A slot may extend through the first sidewall and into communication with the fluid chamber. The slot may include first and second sides and an intermediate gap. An elongated clamping member with a first end and a second end may extend into the outer member and across the slot with the first end on a first side of the slot and the second end on a second side of the slot. The elongated clamping member may be movable to adjust the gap between a first size for the inner member to be movable relative to the outer member to adjust a distance between the first and second contact surfaces, and a second size for the inner member to be fixed relative to the outer member.

The spacer may also include an outer member. The outer member may have a first cavity with an open first end and a cavity wall, a slot that extends through the cavity wall and intersects with the first cavity, a receptacle that extends across the slot with a first section on a first side of the slot and a second section on a second side of the slot, and a first contact surface configured to contact against the first vertebral member. The spacer may also include an inner member. The inner member may have a second contact surface configured to contact against the second vertebral member, and a column having a second cavity. The column may extend through the open first end and into the first cavity, and may have solid walls to contain a fluid. The spacer may include a retaining mechanism that extends into the first and second sections of the receptacle and across the slot to adjust a size of the first cavity. The retaining mechanism may be adjustable between a first position with the first cavity larger than the column for the inner member to be movable relative to the outer member, and a second position to prevent the relative movement between the outer member and the inner member.

The spacer may also include a first contact surface and a second contact surface. A fluid cylinder may be positioned between the first and second contact surfaces and configured to contain a fluid. The fluid cylinder may include an outer cylinder with an open first end that telescopingly receives an inner cylinder. A slot may extend through the outer cylinder at the open first end and intersect with the fluid cylinder. A seal may be positioned in the slot to prevent the fluid from leaking from the fluid cylinder.

DETAILED DESCRIPTION

Figure 1:
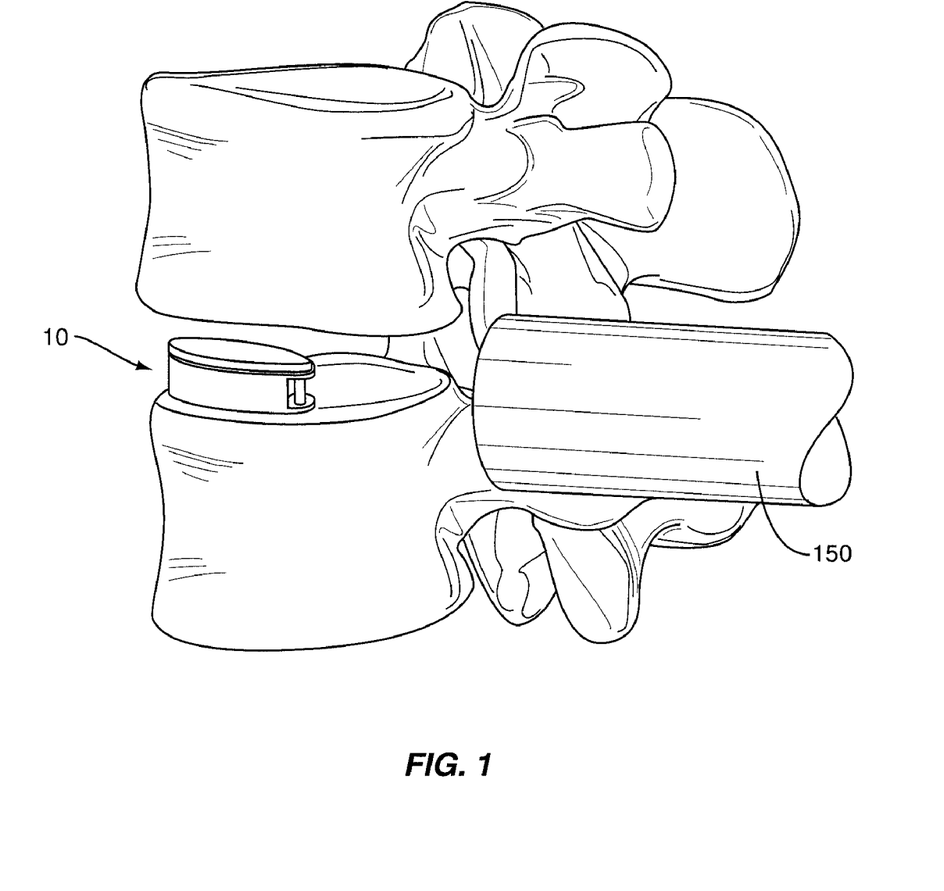
FIG. 1 is a perspective view of an exemplary intervertebral spacer in a retracted position disposed between two vertebral members.
Figure 2:
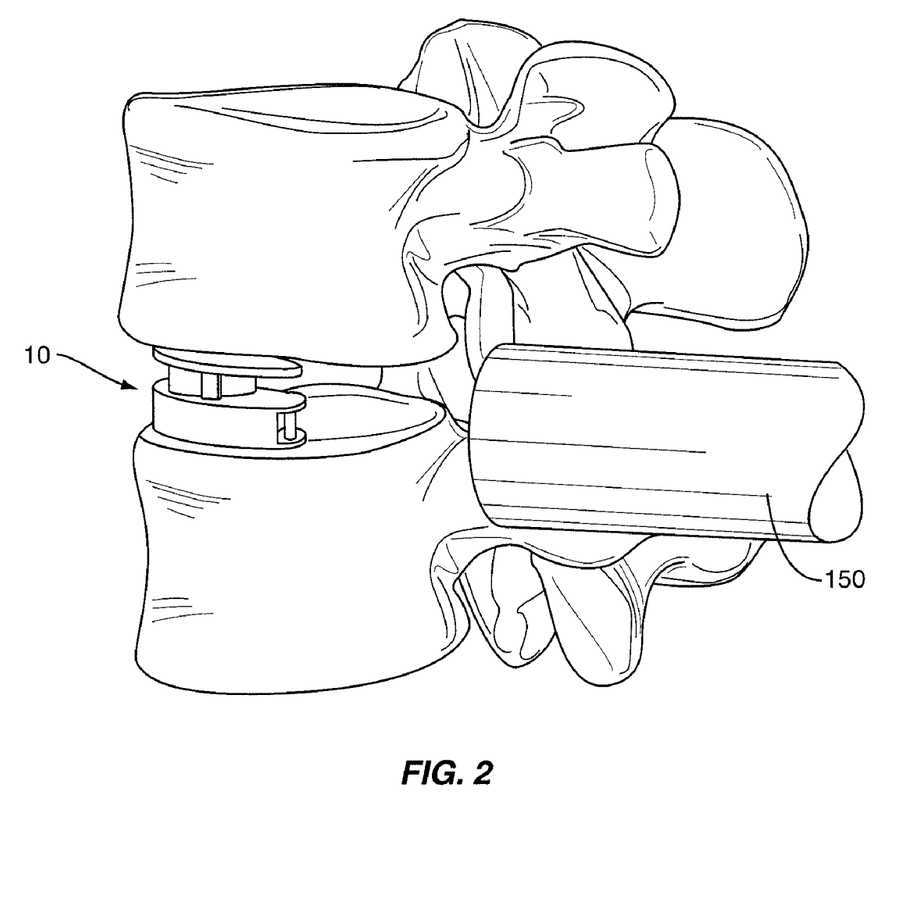
FIG. 2 is a perspective view of an exemplary intervertebral spacer in an extended position disposed between two vertebral members.

The present application relates to implants for replacing an intervertebral disc, vertebral member, or combination of both, and to methods of inserting the same. The implant comprises an intervertebral spacer 10 that can be inserted between vertebral bodies in a compact configuration as shown in FIG. 1 and subsequently expanded to contact the adjacent vertebral bodies as shown in FIG. 2.

Figure 3:
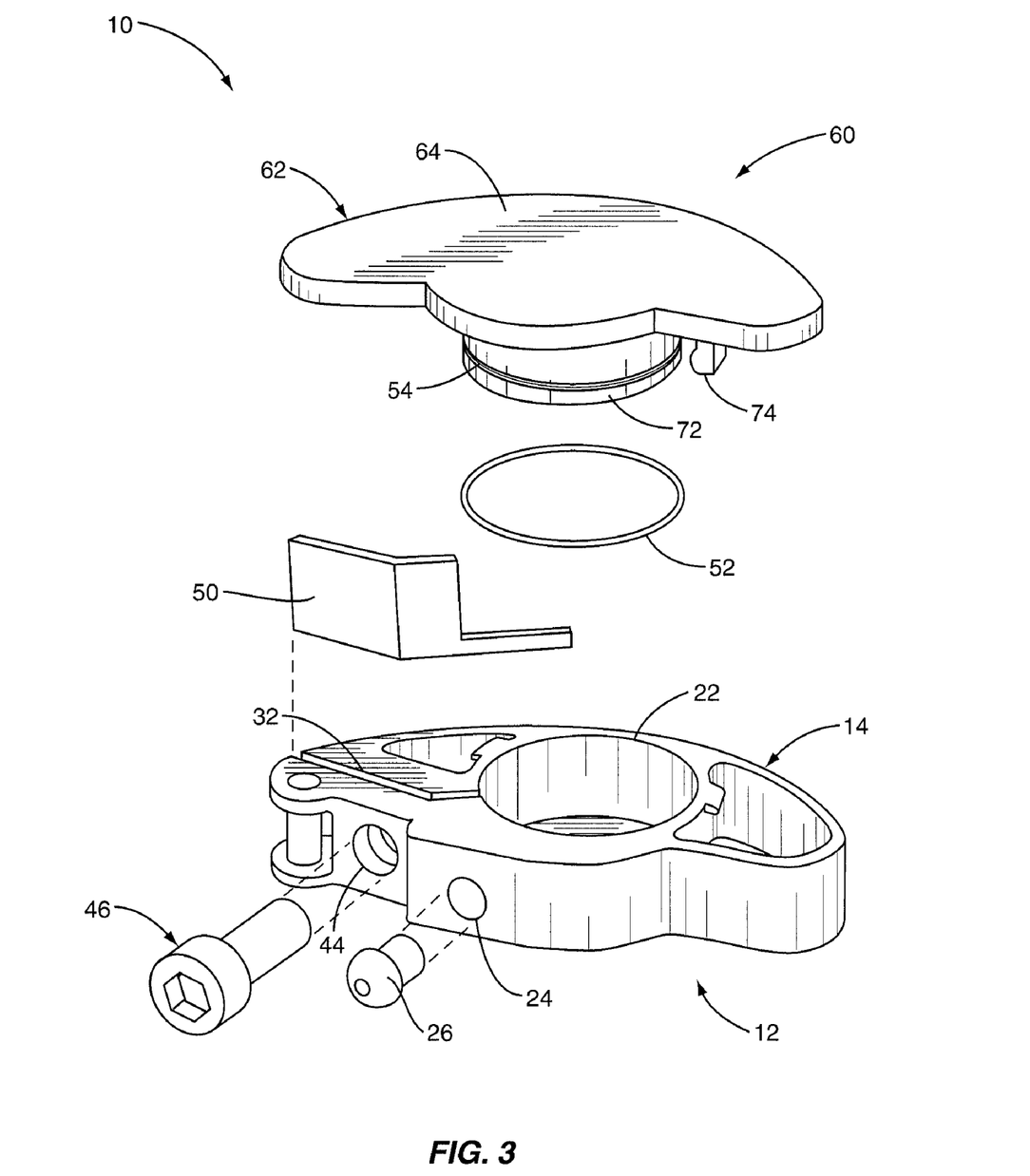
FIG. 3 is an exploded perspective view of an exemplary intervertebral spacer.
Figure 4:
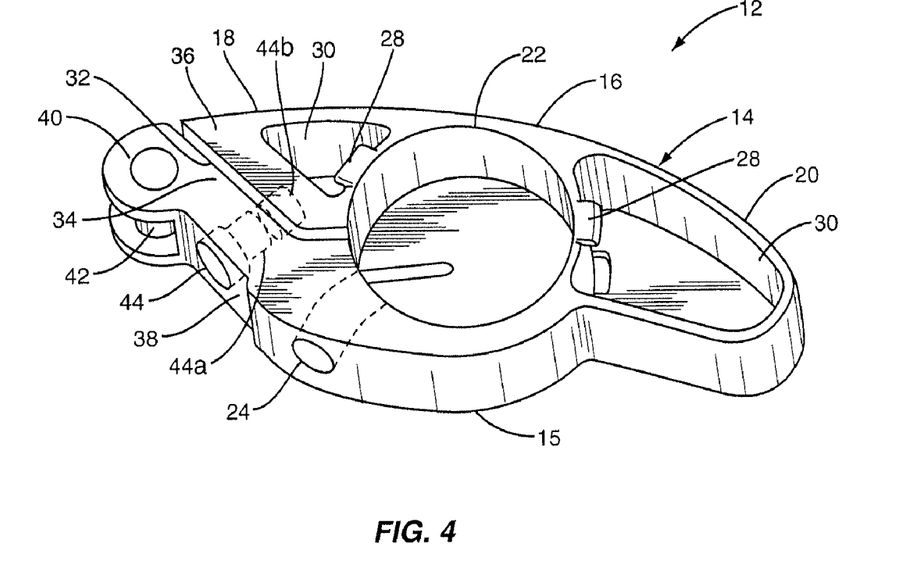
FIG. 4 is a perspective view of an inferior member for an exemplary intervertebral spacer.
Figure 5:
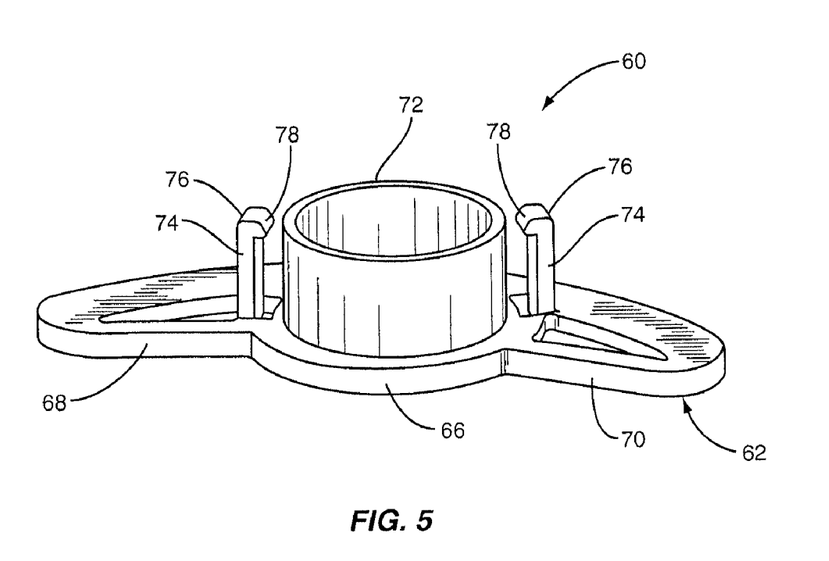
FIG. 5 is a perspective view of a superior member for an exemplary intervertebral spacer.

FIGS. 3-5 illustrate one exemplary embodiment of the intervertebral spacer 10. The intervertebral spacer 10 comprises an inferior member 12 and a superior member 60 movable with respect to the inferior member 12 from a retracted position to an extended position. As will be described in more detail below, the inferior member 12 includes a first cylinder 22, and the superior member 60 includes a second cylinder 72 that is insertable into the first cylinder 22. The cylinders 22 and 72 together define an expansion chamber. When fluid is introduced into the expansion chamber, the superior member 60 is urged away from the inferior member 12. While cylinders 22 and 72 are shown having a circular cross-section, those skilled in the art will appreciate that the cylinders 22 and 72 can have other shapes, such as square, rectangular, oval, kidney-shape, etc.

FIG. 4 illustrates details of one embodiment of the inferior member 12. The inferior member 12 comprises a body 14 including a bottom surface 15 that contacts an adjacent vertebral body. The bottom surface 15 can be textured to grip the vertebral body. For example, teeth, ridges, or grooves can be formed in the bottom surface 15 to improve gripping capability. The body 14 has an oblong configuration including a central section 16 and wing sections 18 and 20. Cylinder 22 is formed in the central section 16. A fluid port 24 is formed in the central section 16 for introducing fluid into the expansion chamber formed by cylinders 22 and 72. A one-way valve 26 (FIG. 3) is disposed in the fluid port 24 that allows introduction of fluid, such as a saline solution, into the expansion chamber, and prevents fluid from exiting the expansion chamber. One or more cavities 30 may be formed in the wing sections 18 and 20 to reduce weight and material requirements.

A slot 32 is formed in the wing section 18. Slot 32 divides the wing section 18 into first and second clamping portions 34 and 36, respectively, and intersects both the wall and bottom of the cylinder 22. A compressible seal 50 is disposed within the slot 32 to prevent fluid from leaking from the expansion chamber. Clamping portion 34 includes a recessed surface 38. A pair of spaced-apart ears 40 project outward from the recessed surface 38 for mounting a pin 42. The ends of the pin 42 are firmly secured in openings formed in the ears 40. Any suitable techniques for securing the pin 42 can be used. A screw hole 44 extends inward from the recessed surface 38 to receive a locking screw 46. The screw hole 44 crosses the slot 32 such that the screw hole 44 is divided into two portions 44a, 44b. Portion 44b of the screw hole 44 is threaded. When the locking screw 46 is tightened, the clamping portions 34 and 36 are pulled together, causing a slight contraction of the cylinder 22. As will be hereinafter described, this clamping arrangement functions as a locking mechanism to lock the superior member 60 firmly in place once proper height adjustment has been made.

The superior member 60, shown in FIG. 5, comprises a plate 62 having a top surface 64 that engages an adjacent vertebral body. The top surface 64 can be textured to grip the vertebral body. For example, small teeth, ridges, or grooves can be formed in the top surface 64 to improve gripping capability. The top plate 62 is shaped to generally correspond to the shape of the inferior member 12. The top plate 62 includes a central section 66 and wing sections 68 and 70. A cylinder 72 extends from the bottom surface of the top plate 62. Cylinder 72 is sized to fit within the cylinder 22 in the inferior member 12. In one embodiment, the interior dimension of the cylinder 22 and exterior diameter of the cylinder 22 are sized to close tolerances such that a seal is formed between the interior wall of cylinder 22 and outer surface of cylinder 72. However, those skilled in the art will appreciate that a ring seal 52 may be used to form a fluid tight seal between cylinders 22 and 72. An annular groove 54 may also be formed in the outer surface of the cylinder 72 to position the seal 52.

A mechanism can be provided to prevent the inferior member 12 and superior member 60 from separating. In one embodiment, a pair of resilient fingers 74 extends downward from the bottom surface of the top plate 62 of superior member 60. The enlarged ends 76 of the resilient fingers 74 are configured to engage the locking tabs 28 on the inferior member 12. When the superior member 60 is assembled with the inferior member 12, the ends of the locking fingers 74 contact the locking tabs 28. Camming surfaces 78 on the enlarged ends 76 of the locking fingers 74 cause the resilient fingers 74 to flex outward and pass over the locking tabs 28. Once the enlarged ends 76 have passed over the locking tabs 28, the resilient fingers 74 return to their original position, thereby preventing separation of the superior member 60. Thus, the resilient fingers 74 and locking tabs 28 cooperate to retain the superior member 60 in place.

Figure 6:
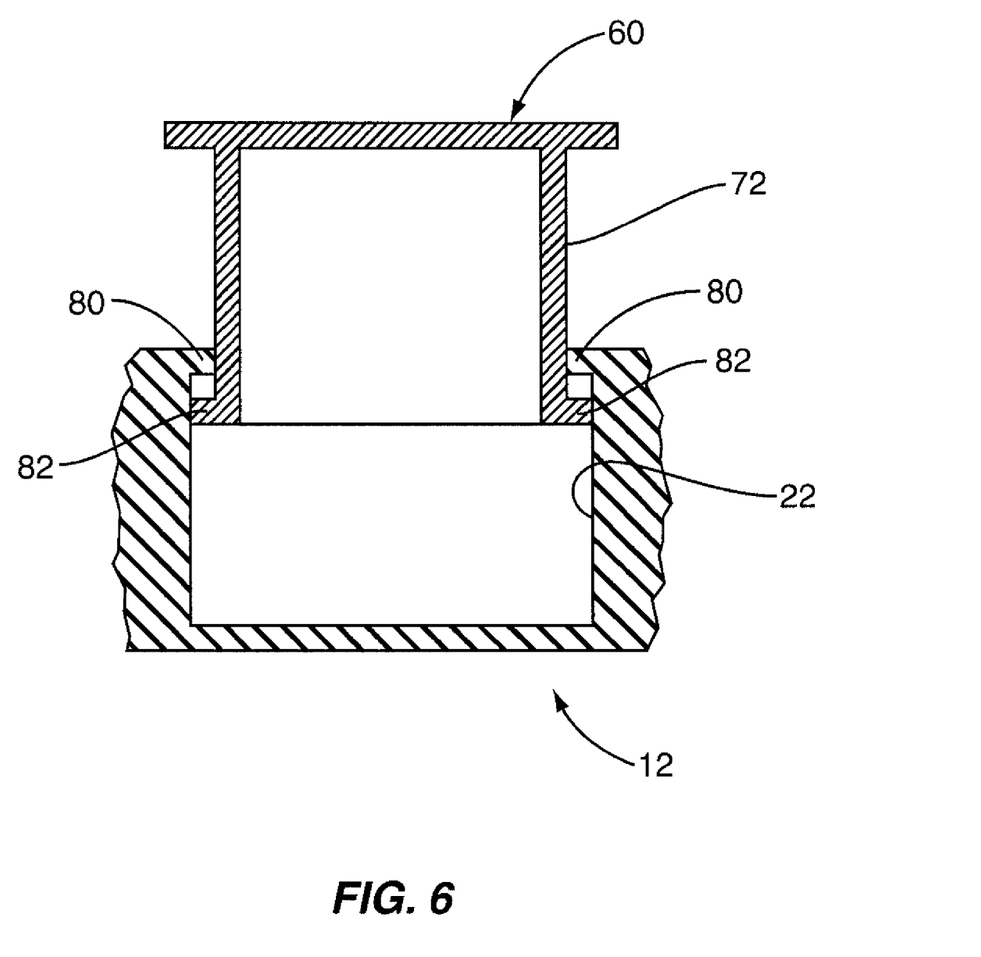
FIG. 6 is a detail view of one exemplary intervertebral spacer.

FIG. 6 illustrates an alternate method of preventing separation of the inferior member 12 and superior member 60. In this embodiment, an inwardly projecting lip 80 is formed at the top end of cylinder 22 and an outwardly projecting lip 82 is formed at the bottom end of cylinder 72. In this embodiment, the superior member 60 can be assembled with the inferior member 12 by dipping the superior member 60 in a cold liquid, such as liquid nitrogen, to shrink the superior member 60. When the superior member 60 shrinks, the lip 82 on cylinder 72 will pass through the lip 80 on cylinder 22. The superior member 60 will then expand to its original size as it returns to ambient temperatures.

The inferior member 12 and superior member 60 can be made of any suitable material, such as PEEK. The bottom of the inferior member 12 and/or top plate 62 of the superior member 60 could be porous to allow the in-growth of bone. An embedded biologic coating, such as hydroxia appetite (HA), BMP, or calcium phosphate could be used to promote bone in-growth. The contact surfaces of the inferior and superior members 12 and 72 could also be textured to grip the adjacent vertebral bodies.

In use, the superior member 60 is assembled to the inferior member 12 and placed in a compact configuration with the superior member 60 in a retracted position relative to the inferior member 12 as shown in FIG. 1. The intervertebral spacer 10, in a compact configuration, is inserted through a cannula 150 into an intervertebral space between two vertebral bodies (FIG. 1). Those skilled in the art will appreciate that the intervertebral spacer 10 can replace one or more disks and/or vertebral bodies. After the insertion of the intervertebral spacer 10, fluid or compressed air is introduced into the expansion chamber to cause the superior member 60 to extend away from the inferior member 12 as shown in FIG. 2. The superior member 60 is raised until the contact surfaces of the inferior and superior members 12 and 60 are engaged with the adjacent vertebral bodies. Once the height of the intervertebral spacer 10 is properly adjusted, the locking screw 24 is tightened to lock the superior member 60 in a fixed position relative to the inferior member 12. Tightening the locking screw 46 causes the cylinder 22 of the inferior member 12 to contract and clamp against the exterior surface of cylinder 22. Thus, the cylinder 22 itself functions as a clamp that will lock the inferior and superior members 12, 60 in position, even in the event that fluid leaks from the expansion chamber.

Figure 7:
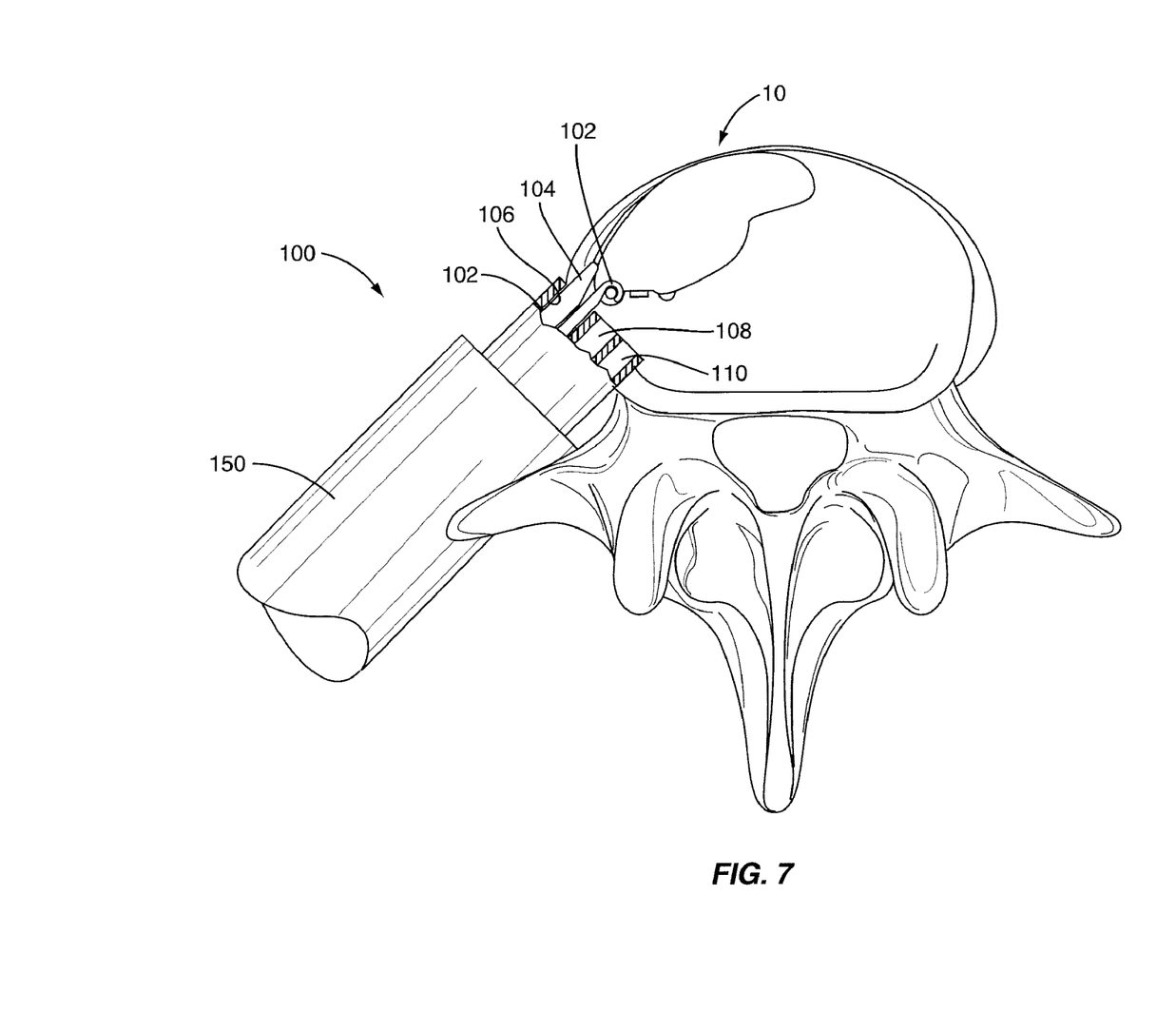
FIGS. 7 and 8 illustrate an exemplary method of inserting the intervertebral spacer.
Figure 8:
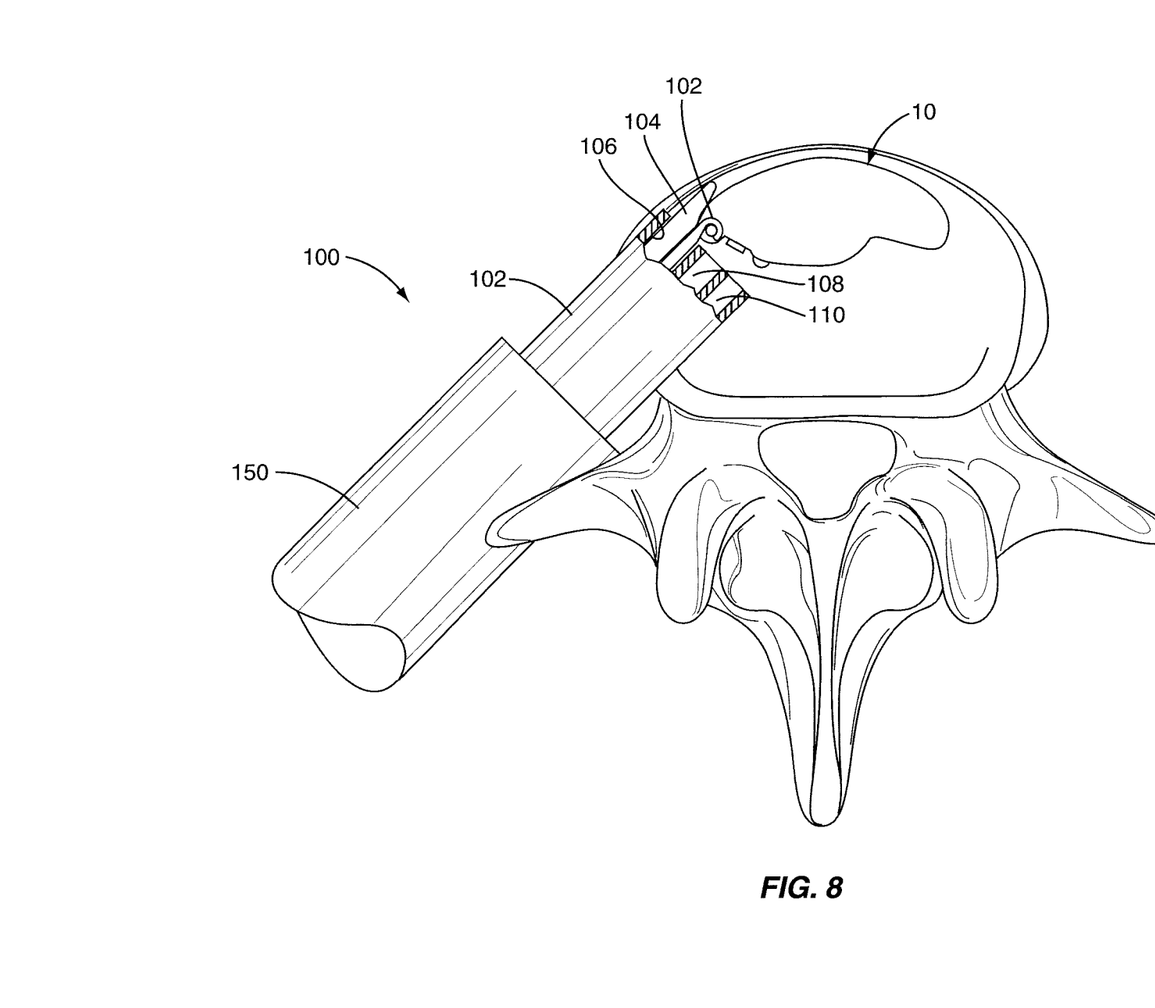

FIGS. 7 and 8 illustrate an exemplary insertion tool 100 to insert the intervertebral spacer 10. The insertion tool 100 includes an elongate housing 102 having three lumens 106, 108, and 110 formed therein. Access to the intervertebral space is gained through a cannula 150 inserted into the body. FIGS. 7 and 8 illustrate the distal end of the cannula 150 and insertion tool 100. The insertion tool 100 includes a hook member 102 that engages pin 42 on the intervertebral spacer 10. As the intervertebral spacer 10 is advanced through the cannula 150, the intervertebral spacer 10 initially assumes the position shown in FIG. 7. When the intervertebral spacer 10 exits from the end of the cannula 150, a push rod 104 is used to rotate the intervertebral spacer 10 into the proper angular position.

The hook member 102 and push rod 104 pass through the first lumen 106. The second lumen 108 aligns with the locking screw 46. The third lumen 110 aligns with the fluid valve 26. After the intervertebral spacer 10 is properly positioned, a fluid delivery line can be inserted through lumen 110 and engaged with the fluid valve 26 to deliver fluid into the expansion chamber to expand the intervertebral spacer 10. A tool can then be inserted through the middle lumen 108 to tighten the locking screw 42.

The embodiments described above include member 60 being a superior member and member 12 being inferior. In another embodiment, the orientation of these members 60, 12 may be interchanged with member 60 functioning as an inferior member and member 12 functioning as a superior member.

One embodiment includes accessing the spine from a postero-lateral approach. Other applications contemplate other approaches, including posterior, anterior, antero-lateral and lateral approaches to the spine, and accessing other regions of the spine, including the cervical, thoracic, lumbar and/or sacral portions of the spine.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An intervertebral spacer for positioning between first and second vertebral members comprising:
    a first contact surface to contact the first vertebral member;
    a second contact surface to contact the second vertebral member;
    a fluid chamber positioned between the contact surfaces and having telescoping inner and outer members with the outer member having a first sidewall and being sized to receive the second member;
    a slot extending through the first sidewall and into communication with the fluid chamber, the slot including first and second sides and an intermediate gap;
    an elongated clamping member having a first end and a second end, the clamping member extending into the outer member and across the slot with the first end on a first side of the slot and the second end on a second side of the slot;
    the elongated clamping member movable to adjust the gap between a first size for the inner member to be movable relative to the outer member to adjust a distance between the first and second contact surfaces, and a second size for the inner member to be fixed relative to the outer member.

2. The intervertebral spacer of claim 1, wherein the slot extends from an exterior surface of the outer member through the sidewall and into the fluid chamber.

3. The intervertebral spacer of claim 1, wherein the inner member includes continuous walls to contain a fluid and an open end, the open end faces towards the outer member.

4. The intervertebral spacer of claim 1, further comprising an inlet that extends through one of the inner and outer members and into the fluid chamber, the inlet being spaced away from the slot.

5. The intervertebral spacer of claim 1, wherein the elongated clamping member is a screw with the first end including a head and the second end including having a tip, the screw further including threads positioned between the head and the tip.

6. The intervertebral spacer of claim 1, further comprising a retaining mechanism spaced away from the fluid chamber to prevent the inner member from separating from the outer member, the retaining mechanism including one or more resilient fingers on either the inner or outer member that engage with one or more tabs on the other of the inner and outer member.

7. The intervertebral spacer of claim 1, further comprising a seal positioned in the gap between the first and second sides of the slot, the seal configured to prevent fluid from escaping into the slot from the fluid chamber.

8. An intervertebral spacer for positioning between first and second vertebral members comprising:
    an outer member having:
        a first cavity with an open first end and a cavity wall;
        a slot that extends through the cavity wall and intersects with the first cavity, the slot being formed between first and second walls;
        a receptacle that extends across the slot with a first section in the first wall on a first side of the slot and a second section in the second wall on a second side of the slot; and
        a first contact surface configured to contact against the first vertebral member;
    an inner member having:
        a second contact surface configured to contact against the second vertebral member; and
        a column having a second cavity, the column extends through the open first end and into the first cavity, the column having solid walls for the second cavity to contain a fluid;
    a retaining mechanism that extends into the first and second sections of the receptacle and across the slot to adjust a size of the first cavity, the retaining mechanism adjustable between a first position with the first cavity larger than the column for the inner member to be movable relative to the outer member, and a second position to prevent the relative movement between the outer member and the inner member.

9. The intervertebral spacer of claim 8, wherein the slot intersects with the open first end of the first cavity.

10. The intervertebral spacer of claim 9, wherein the slot extends along the cavity wall from the open first end to a bottom of the first cavity.

11. The intervertebral spacer of claim 8, wherein the cavity wall of the first cavity and the column are positioned in an overlapping arrangement.

12. The intervertebral spacer of claim 8, wherein the receptacle includes threads and the retaining mechanism is a screw with a threaded shaft that engages with the threads.

13. The intervertebral spacer of claim 8, further comprising an inlet that leads into a fluid chamber formed by the first and second cavities, the inlet being spaced away from the slot.

14. The intervertebral spacer of claim 8, further comprising a seal positioned in the slot to prevent fluid from escaping into the slot from the first and second cavities.

15. The intervertebral spacer of claim 8, further comprising a second seal that extends around an exterior of the column.

\* \* \* \* \*